US005908862A

United States Patent [19]

[11] Patent Number: 5,908,862

Wai Lee et al.

[45] **Date of Patent: *Jun. 1, 1999**

[54] WATER-MISCIBLE ESTERS OF MONO— AND DIGLYCERIDES HAVING ANTIBACTERIAL ACTIVITY AND THEIR USE IN INHIBITING INFECTION

[75] Inventors: Theresa Siu-Ling Wai Lee; Joseph Schaller, both of Columbus, Ohio; Steven N. Anderson, Aurora, Ill.; Terry Bruce Mazer, Reynoldsburg, Ohio; Milo Duane Hilty, Lewis Center, Ohio; Melinda Guzman-Harty, Gahanna, Ohio; Jonathan Allan Meulbroek, Lake Forest, Ill.; Patricia Joan Ewing, McHenry, Ill.; Jin-Zhou Liu, Westerville, Ohio

[73] Assignee: Abbot Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,742

[22] Filed: Jul. 31, 1996

[51] Int. Cl.[6] .................................................... A61K 31/22

[52] U.S. Cl. .......................... 514/546; 514/547; 514/548; 514/549; 514/558; 514/559; 514/560

[58] Field of Search .................................... 514/546, 547, 514/548, 549, 558, 559, 560

[56] References Cited

U.S. PATENT DOCUMENTS

| | | | |
|---|---|---|---|
| 2,236,516 | 11/1941 | Cahn et al. | 554/148 |
| 3,443,965 | 5/1969 | Birnbaum | 426/654 |
| 3,978,099 | 8/1976 | Tuma | 554/148 |
| 4,002,775 | 1/1977 | Kabara | 426/532 |
| 4,146,548 | 3/1979 | Forsythe | 260/410.6 |
| 4,446,165 | 5/1984 | Roberts | 426/602 |
| 4,497,800 | 2/1985 | Larson et al. | 514/2 |
| 5,560,904 | 10/1996 | Laugier | 424/78.08 |

FOREIGN PATENT DOCUMENTS

| | | |
|---|---|---|
| 0 626 175 | 11/1994 | European Pat. Off. . |
| 0 626 177 | 11/1994 | European Pat. Off. . |
| WO 94/26129 | 11/1994 | WIPO . |
| WO 95/31956 | 11/1995 | WIPO . |

OTHER PUBLICATIONS

Chemical Abstracts (123:168286) Murata et al. (1995).

Abstract of Japanese Patent Publication No. 07008238 (1995).

Abstract of Japanese Patent Publication No. 58067170 (1983).

Abstract of Japanese Patent Publication No. 02188504 (1990).

Abstract of Japanese Publication No. 0401 6230 (1992).

Chemical Abstracts, vol. 81, No. 7, Aug. 19, 1974, Abstract No. 37755.

Chem. Abstracts, 124:66212—Laugier (1994).

Kabara, J. "The Pharmacological Effects of Lipids," ed. 1987, Nutritional Biochemistry, vol. 6, Jul. 1995.

Isaacs, et al., "Antimicrobial Activity of Lipids Added to Human Milk, Infant Formula, and Bovine Milk," Nutritional Biochemistry, 1995.

Larssen, et al. eds., "Food Emulsions," Publ. Marcel Dekker, Inc., 1990, Appendix Tables, pp. 2198–2247.

Danisco Ingred. USA, p. from catalog titled Diacetyl Tartaric Acid Esters (DATEM) and bearing a facsimile date of Jun. 14, 1996.

Geelen, et al., "The Cell Wall Mediates Pneumoccoccal Attachment to and Cytopathology in Human Endothelial Cells," Infection and Immunity, vol. 61, No. 4, Apr. 1993, p. 1538–1543.

Cundell, et al., "Relationship Between Colonial Morphology and Adherence of *Streptococcus pneumoniae,*" Infection and Immunity, vol. 63, No. 3, Mar. 1995, pp. 757–761.

Prince, et al., "Mechanisms of Immunity to Respiratory Syncytial Virus in Cotton Rats," Infection and Immunity, Oct. 1983, p. 81–87.

Porter, et al., Pathogenesis of Human Parainfluenza Virus 3 Infection in Two Species of Cotton Rats: *Sigmodon hispidus* Develops Bronchiolitis, While *Sigmodon fulviventer* Develops Interstitial Pneumonia, J. of Virology, Jan. 1991, pp. 103–111.

Stauffer, C., "Fats and Oils," Eagan Press, May 13, 1996, pp. 42–43.

*Primary Examiner*—Kevin E. Weddington

*Attorney, Agent, or Firm*—Thomas D. Brainard; J. Michael Dixon

[57] ABSTRACT

A process of treating a bacterial infection in a subject in need of such treatment including the step of administering to the subject an effective bactericidal amount of diacetyltartaric acid esters of mono- and diglycerides is provided. Pharmaceutical compositions containing diacetyltartaric acid esters of mono- and diglycerides as an active bactericidal agent are also provided.

21 Claims, No Drawings

WATER-MISCIBLE ESTERS OF MONO— AND DIGLYCERIDES HAVING ANTIBACTERIAL ACTIVITY AND THEIR USE IN INHIBITING INFECTION

CROSS REFERENCE TO RELATED APPLICATIONS

The present application is related to "Nutritional Formulations Containing Water-Miscible Lipid Derivatives As Antibacterial Agents", which corresponds to Ser. No. 690,737 and was filed on Jul. 31, 1996, "Nutritional Formulations Containing Water-Miscible Lipid Derivatives As Antimicrobial Agents", which corresponds to Ser. No. 690,736 and was filed on Jul. 31, 1996, "Water-Miscible Esters Of Monoglycerides Having Antimicrobial Activity", which corresponds to Ser. No. 690,492 and was filed on Jul. 31, 1996, and "Water-Miscible Esters Of Mono- And Diglycerides Having Antimicrobial Activity And Their Use In Inhibiting Infection", which corresponds to Ser. No. 690,742 and was filed on Jul. 31, 1996, all of which are filed concurrently herewith, and the text of all of which are herein incorporated by reference.

TECHNICAL FIELD OF THE INVENTION

The present invention relates generally to pharmaceutical compositions containing water-miscible lipid derivatives as active bactericidal agents and to methods of using such compositions to treat or prevent bacterial infection.

BACKGROUND OF THE INVENTION

It has been previously reported (Kabara, *The Pharmacological Effects of Lipids*, ed. 1987, and *Nutritional Biochemistry*, Vol. 6, July, 1995) that certain lipids have antimicrobial (anti-bacterial and anti-viral) effects. Those lipids reported to have anti-microbial activity are highly lipophilic, have HLB values of 2 to 4 and likely act by affecting the infectious organism's lipid envelope or membrane leading to changes in the organism's permeability resulting in loss of infectivity.

The high lipophilicity of those lipids, however, makes it difficult to carry out prophylactic and therapeutic studies because the lipids are insoluble in aqueous solutions. The solubility problems can be overcome to some extent through the use of non-aqueous solvents such as ethanol or dimethylsulfoxide (DMSO) (Isaacs, Litov, and Thormar, *Nutritional Biochemistry,* 1995). Such solvents, in many instances, are inappropriate for use in humans or animals. By way of example, ethanol and DMSO are contraindicated for use in infants.

Still another problem associated with the use of existing antimicrobial lipids is that the antimicrobial action is inhibited or greatly reduced in the presence of proteins (Kabara, *The Pharmacological Effects of Lipids*, ed. 1987; and U.S. Pat. No. 4,002,775, *Fatty Acids and Derivatives as Antimicrobial Agents,* 1977). Thus, such lipids cannot be administered together with proteins such as are present in enteral nutritional formulations. There continues to be a need in the art therefore for antimicrobial lipids that are soluble in aqueous formulations and those that are not adversely affected by intact protein.

BRIEF SUMMARY OF THE INVENTION

The present invention provides a pharmaceutical composition that contains an effective bactericidal amount of water-miscible lipid derivatives. Preferred water-miscible lipid derivatives are diacetyltartaric acid esters of mono- and diglycerides. The diacetyltartaric acid esters of mono- and diglycerides can be those used as GRAS emulsifiers and known as DATEMs or can be novel such esters wherein 90 percent or more of the fatty acid content is accounted for by a single fatty acid. Where the latter forms of diacetyltartaric acid esters of mono- and diglycerides are used, the fatty acid component preferably contains from 8 to 24 and, more preferably, from about 10 to about 20 carbon atoms. The fatty acid can be saturated, unsaturated or hydroxylated. A pharmaceutical composition of the present invention can further include antibacterial or antiviral amounts of lipophilic lipids having an HLB value of less than about 6.

The present invention further provides a process of inhibiting a bacterial infection in a subject in need of such treatment. In accordance with that process the subject is administered an effective amount of diacetyltartaric acid esters of mono- and diglycerides.

DETAILED DESCRIPTION OF THE INVENTION

I. Pharmaceutical Composition

The present invention provides a pharmaceutical composition that contains an amount of a water-miscible lipid derivative that is effective to inhibit the infectious activity of bacteria together with a physiologically acceptable diluent. The water-miscible lipid derivative comprises a lipophilic moiety linked via an ester or ether linkage to a hydrophilic moiety. The lipophilic moiety comprises a fatty acid, a monoacylglycerol (monoglyceride), a diacylglycerol (diglyceride), a monoetherglycerol derivative, or a dietherglycerol derivative. The hydrophilic moiety comprises an organic acid, an organic alcohol or a salt thereof.

In one embodiment, the water-miscible lipid derivative is a mono/diglyceride wherein one or two of the glycerol carbon atoms are linked to an alkyl or acyl group and at least one of the remaining glycerol carbon atoms is linked via an ester linkage to an organic acid. In a preferred embodiment, the organic acid is tartaric acid that has been derivatized with acetyl groups. In accordance with this embodiment, the water-miscible lipid derivatives are diacetyltartaric acid esters of mono- and diglycerides.

Certain of such diacetyltartaric acid esters of mono- and diglycerides are known in the art as DATEMs and are GRAS emulsifiers for foodstuffs. DATEMs are formed by reacting diacetyltartaric anhydride with partial glycerides of edible oils, fats or fat-forming fatty acids. Sources of glycerides for the production of DATEMs include soy oil, palm oil, sunflower oil, beef tallow and monoglycerides. DATEMs can also be obtained from commercial sources. For example, DATEM SOY, Panodan FDP Kosher (derived from fully hydrogenated soybean oil) DATEM SUNF, SDK (derived from unhydrogenated sunflower 2 0 oil), DATEM-C12 (derived from 90% $C_{12}$ monoglyceride) and DATEM-C08 (derived from 90% $C_8$ monoglyceride), are commercially available from Danisco Ingredients, Grinsted Division.

In another embodiment, the water-miscible lipid derivative corresponds to Formula I, below.

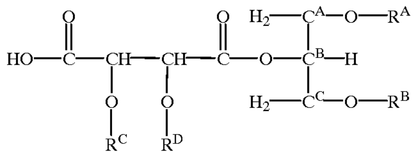

In formula I, each of $R^A$ and $R^B$ can independently be hydrogen, an acyl group having from 6 to 26 carbon atoms ($C_6$–$C_{26}$ acyl), an alkyl group having from 6 to 26 carbon atoms ($C_6$–$C_{26}$ alkyl), or an inorganic anion. Exemplary such anions are halides, nitrates, sulfates and phosphates. The acyl and alkyl groups can be saturated, unsaturated or hydroxylated. Preferably, the acyl and alkyl groups have from 8 to 24 carbon atoms and, more preferably from 10 to 20 carbon atoms. $R^A$ and $R^B$ can link to any of the $C^A$, $C^B$ or $C^C$ carbons of the glycerol backbone. Similarly, the organic acid moiety (shown as tartaric acid in Formula I) can link to any of the $C^A$, $C^B$ or $C^C$ carbons not linked to an acyl or alkyl group. One of ordinary skill in the art will recognize that other organic acids can be used in place of tartaric acid. Each of $R^C$ and $R^D$ can independently be an acyl or an alkyl group containing from 2 to 6 carbon atoms, which groups can be saturated, unsaturated or hydroxylated. Exemplary $R^C$ and $R^D$ groups are acetyl and succinyl esters. In a compound of Formula I, 90 percent or more of the total fatty acid content is in the form a single fatty acid.

Where only one of $R^A$ or $R^B$ is an acyl group, the molecule is a monoacylglycerol (or monoglyceride) derivative. Where both of $R^A$ and $R^B$ are acyl groups, the molecule is a diacylglycerol (or diglyceride) derivative. Where only one of $R^A$ or $R^B$ is an alkyl group, it is a monoetherglycerol derivative, and if both $R^A$ and $R^B$ are alkyl groups, it is a dietherglycerol derivative. It is possible that the $R^A$ and $R^B$ can be one acyl group and one alkyl group. The linkage for the acyl group to the glycerol backbone is an ester linkage, and the linkage for the alkyl group to the glycerol backbone is an ether linkage.

In a preferred embodiment of Formula I, $R^A$ is a $C_8$–$C_{24}$ acyl, $R^B$ is hydrogen, $R^C$ and $R^D$ are both acetyl and the lipids are diacetyltartaric acid esters of monoglycerides.

As used herein, the term "DATEM" will be used to mean those lipids known in the art as GRAS emulsifiers and which lipids have been approved as emulsifiers by the FDA and the EEC. These DATEMs are characterized by containing a mixture of fatty acids. As used herein, the phrase "diacetyltartaric acid esters of mono- and diglycerides" means DATEMs as well as novel lipids as defined above by Formula I.

Diacetyltartaric acid esters of mono- and diglycerides are made using standard techniques well known in the art (See, e.g., Schuster and Adams, Rev. Fr. Corps Gras, 29(9):357–365, 1981). Diacetyltartaric acid esters of mono- and diglycerides, produced either from glycerides of edible fats or from fatty acids can exist in a variety of isomer forms (See, e.g., Food Emulsions, Second Edition, Revised and Expanded, ed. by Larsson and Friberg, Marcel Dekker, Inc., New York, 1990). Thus, a lipid of Formula I can exist in different isomeric forms.

In another embodiment, the water-miscible lipid is a modified glyceride such as a fatty acid acyl lactylate or a salt thereof. Particular such lactylates (e.g., sodium stearoyl-2-lactylate) are well known GRAS emulsifiers, stabilizers and dough conditioners. The fatty acid component of the lactylate can be any fatty acid and is not limited to stearic acid. A preferred fatty acid component of a lactylate is lauric acid. Fatty acid acyl lactylates can be made using standard procedures well known in the art (See, e.g., U.S. Pat. No. 4,146,548, the disclosure of which is incorporated herein by reference).

The diacetyltartaric acid esters of mono- and diglycerides are formulated into compositions together with one or more non-toxic physiologically tolerable or acceptable diluents, carriers, adjuvants or vehicles that are collectively referred to herein as diluents, for administration to subject. The compositions can be administered to humans and animals either orally, locally (powders, ointments or drops), as a nasal spray or as a suppository.

Suitable pharmaceutical composition may comprise physiologically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An especially preferred pharmaceutical composition contains diacetyltartaric acid esters of mono- and diglycerides dissolved in an aqueous medium or solvent. Diacetyltartaric acid esters of mono- and diglycerides have an HLB value of about 9–12 and are significantly more hydrophilic than existing antimicrobial lipids that have HLB values of 2–4. Those existing hydrophobic lipids cannot be formulated into aqueous compositions. As disclosed herein, those lipids can now be solubilized in aqueous media in combination with diacetyltartaric acid esters of mono- and diglycerides. In accordance with this embodiment, diacetyltartaric acid esters of mono- and diglycerides (e.g., DATEM SOY, Panodan) are melted with other active antimicrobial lipids (e.g., 18:2 and 12:0 monoglycerides) and mixed to obtain a homogeneous mixture. Homogeneity allows for increased activity. The mixture can be completely dispersed in water. This is not possible without the addition of diacetyltartaric acid esters of mono- and diglycerides and premixing with other monoglycerides prior to introduction into water. The aqueous composition can then be admixed under sterile conditions with physiologically acceptable diluents, preservatives, buffers or propellants as may be required to form a spray or inhalant.

Actual dosage levels of diacetyltartaric acid esters of mono- and diglycerides ingredients in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

II. Process of Inhibiting Infection by Bacteria

In another aspect, the present invention provides a process of inhibiting an infection caused by a bacteria in a subject in need of such treatment. In accordance with that process, the subject is administered an amount of a water-miscible lipid effective to inhibit the infectious activity of the bacteria. Preferred such lipids are the same as set forth above. In a preferred embodiment, the hydrophilic lipids are administered to the subject in a pharmaceutical composition that comprises an aqueous solvent that optionally contains bactericidal or virucidal amounts of lipophilic lipids having an HLB value of less than about 6. A preferred subject is a human.

As used herein, the term "inhibit" means treat or prevent. The diacetyltartaric esters are shown herein to particularly effective in inhibiting infections of the upper gastrointestinal tract, the respiratory tract or the ear. As used herein the term "upper gastrointestinal tract" means the mouth, throat, esophagus, stomach and duodenum. As used herein the term "respiratory tract" means the nose, sinuses, eustachian tube, middle ear, mouth, throat, trachea and other airways and the lung (including the alveoli). A process of the present invention has particular utility in inhibiting bacterial infections of the nose, mouth, sinuses, throat, middle ear, stomach and lung.

As described in detail in the Examples to follow, diacetyltartaric acid esters of mono- and diglycerides are effective bactericides against infections caused by a wide range of bacteria, including gram-positive and gram-negative bacteria. Exemplary such bacteria are members of the genus Streptococcus, Haemophilus, Helicobacter, Staphylococcus, Enterococcus, Micrococcus, Enterobacter, Klebsiella, Providensia, Pseudomonas, Acinetobacter, Candida, Mycobacterium, Nocardia, and Eschericia. Exemplary particular bacteria are *S. aureus, S. epidermis, S. bovis, S. agalactiae, S. pyogenes, M. luteus, P. aeruginosa, M. smegmatis, N. asteroides, S. pneumoniae, H. influenzae*, and *H. pylori.*

*Streptococcus pneumoniae* (*S. pneumoniae*) is a gram-positive coccus that usually initiates infection by colonization of the nasopharynx followed by aerosolized spread to the respiratory tract. Clinical manifestations include localized and systemic infections including otitis media, pneumonia, sepsis and meningitis (Geelen, Bhattacharyya, and Tuomanen, *Infection and Immunity,* 1993; Cundell, Weiser, Shen, Young, and Tuomanen, *Infection and Immunity,* 1995). Additionally, *S. pneumoniae* is the single most frequent cause of otitis media (OM), a common and significant illness in infants and children that accounts for more than one third of office visits to pediatricians (Thoene and Johnson, 1991; Kaleida, Nativio, Chao, and Cowden, *Jr. of Clinical Microbiology,* 1993). Haemophilus influenzae (*H. influenzae*) is another common bacterial agent known to cause otitis media in infants and young children. *Helicobacter pylori* (*H. pylori*) is a microaerophilic gram-negative bacterium that infects 50% of the population at age 60 in the US (Blaser, Clinical Infectious Diseases, 1992), and 90% of children by age 5 in the developing countries (Thomas et al., Lancet, 1992). *H. pylori* is a major cause of gastritis, plays a key role in the etiology of peptic ulcer and is a risk factor for gastric cancer.

The water-miscible lipid derivatives are preferably administered in a form and via a route that delivers them most directly to the site of the infection. By way of example, where the bacterial infection is localized predominantly in the nose, ears, mouth or lungs, a preferred formulation is an aerosol, a mouthwash or rinse, chewing gum or a drop formulation administered directly into the mouth or nasal cavity. Where the infection is predominantly localized in the stomach, a liquid or reconstituted powder oral formulation is preferred. Where the infection is localized to the skin, a preferred formulation is an ointment, lotion or other topical formulation. When the infection is localized in the lower gut, a preferred formulation is a suppository. All such formulations are well known in the art.

The following Examples illustrate preferred embodiments of the present invention and are not limiting of the claims and specification in any way.

EXAMPLE 1

Bactericidal Effects of Diacetyltartaric Acid Esters of Mono- and Diglycerides on *S. pneumoniae*

Bactericidal Assay

*Streptococcus pneumoniae* (*S. pneumoniae*) (strain 6303, American Type Culture Collection, Rockville, Md.) was cultured overnight on TSA II (with 5% Sheep Blood) agar plates and harvested at approximately 18 hours using 10 ml of sterile Dulbecco's Phosphate buffered saline (D-PBS). The bacterial suspension was centrifuged at 595×g for 15 minutes at room temperature. The supernatant was discarded and the pellet re-suspended in 2 ml of sterile D-PBS. The re-suspended bacterial suspension was pipetted into two sterile microcentrifuge vials and centrifuged for 4 minutes using an Eppendorf microcentrifuge (8800×g). The supernatant was discarded and the bacterial pellet was resuspended in 2 ml of sterile PBS.

The bacterial count was typically $10^9$ colony forming units (CFU)/ml. 180 $\mu$l of each test product or control was added to sterile microcentrifuge vials followed by 20 $\mu$l of the *S. pneumoniae suspension (*9 parts infant formula: 1 part bacterial suspension). Each vial was mixed and incubated for 1 hour at 37° C. 100 $\mu$l of each test product was then plated on TSA II agar and the inoculum spread over the agar surface.

The inoculum was quantitated by serially diluting the initial bacterial suspension to a final dilution of $10^{-4}$, $10^{-5}$, $10^{-6}$, $10^{-7}$, and $10^{-8}$ and plated on TSA II agar. The plates were then inverted and incubated at 37° C./$CO_2$ 5% incubator for 18 to 24 hours. Growth of bacteria was recorded as growth versus no growth for each of the variables. In some assays, the formula-bacterial suspension ratio was changed to 6.6 parts infant formula to 3.3 parts bacterial suspension changing the final protein concentration in the assay from 13.5 to 9.9 mg/mL.

Test Agents

Monoglyceride C12:0, was obtained from Grinsted Division of Danisco containing a minimum of 90% monoester of C12:0. DATEM SOY, Panodan FDP Kosher was obtained from Danisco Ingredients, Grinsted Division. It is derived from fully hydrogenated soybean oil (U.S. DATEM SPECIFICATIONS). DATEM SUNF, SDK was obtained from Danisco Ingredients, Grinsted Division. SDK is derived from unhydrogenated sunflower oil (U.S. DATEM SPECIFICATIONS). DATEM-C12 was obtained from Danisco Ingredients and is derived from 90% C12 monoglyceride. DATEM-C08 was obtained from Danisco Ingredients and is derived from 90% $C_8$ monoglyceride which was obtained from Hullis America.

The results of these studies are summarized below in Tables 1 and 2.

TABLE 1

*S. PNEUMONIAE* BACTERICIDAL ASSAY IN DILUTE INFANT FORMULA (9.9 MG PROTEIN/ML)

| TREATMENT | FINAL CONCENTRATION OF DATEM in $\mu$g/ml | LOG REDUCTION[a] |
|---|---|---|
| INFANT FORMULA CONTROL | 0 | 0 |
| DATEM SUNF | 2400 | 4.3 |
| DATEM-C12 | 2400 | 4.9 |
| DATEM-C08 | 2400 | 2.4 |

[a]Log reduction is the reduction of bacteria titer in $\log_{10}$. The *S. pneumoniae* inoculum was 4.9 $\log_{10}$.

TABLE 2

*S. PNEUMONIAE* BACTERICIDAL ASSAY IN INFANT FORMULA (13.5 MG PROTEIN/ML)

| TREATMENT | FINAL CONCENTRATION OF DATEM in μg/ml | LOG REDUCTION |
|---|---|---|
| INFANT FORMULA CONTROL | 0 | 0 |
| DATEM SOY | 3300 | 0 |
| DATEM SUNF | 3300 | 0 |
| DATEM C12 | 3300 | 6.8 |
| DATEM-C08 | 3300 | 0 |
| $C_{12}$ MONOGLYCERIDE | 4500 | 0 |

The *S. pneumoniae* inoculum was 6.8 $log_{10}$.

The data from Tables 1 and 2 show that diacetyltartaric acid esters of mono- and diglycerides are effective as *S. pneumoniae* bactericidal agents in an aqueous enteral formulation. The data also show that the bactericidal action of diacetyltartaric acid esters of mono- and diglycerides is not adversely affected by the presence of protein. Each of the diacetyltartaric acid esters of mono- and diglycerides tested at lower protein concentrations (9.9 mg/ml) had significant bactericidal activity versus *S. pneumoniae*. Only DATEM-C12 produced from $C_{12}$ monoglyceride demonstrated bactericidal activity at protein concentrations normally found in infant formula at an inoculum of 6.8 $log_{10}$.

Animal Studies

Neonatal (24 hours-old) rats (10 rats per group) were inoculated with various test samples containing one of two strains of *S. pneumoniae* (Sp DB31 and Sp DB40 at 5.72 and 4.74 $log_{10}$ inoculum dose, respectively). These mixtures were incubated at 37° C. for one hour before intranasal inoculation. Nasopharyngeal lavage fluid of the rat was collected 24 hours after *S. pneumoniae* inoculation and analyzed for *S. pneumoniae* population. Three different test samples were studied: Similac® RTF alone as a control; DATEM-C12 added to the basic control at 3650 mg/L, and DATEM-C12 (1825 mg/L) and sunflower monoglyceride (5000 mg/L). The results from these animal studies are summarized below in Table 3.

TABLE 3

DATEM INHIBITS *S. PNEUMONIAE* INFECTION IN NEONATAL RATS

| Treatment | Sp strain DB31 | Sp strain DB40 |
|---|---|---|
| | $Log_{10}$ CFU/ml | |
| SIM RTF (Control) | 5.75 ± 0.10 | 6.29 ± 0.26 |
| DATEM-C12 (3650 ppm) | 3.75 ± 0.94 | 2.57 ± 0.70 |
| DATEM-C12 + MG (1825 ppm + 5000 ppm) | 0.00 ± 0.00 | 0.66 ± 0.45 |

The data from Table 3 show that diacetyltartaric acid esters of mono- and diglycerides alone are effective in suppressing *S. pneumoniae* infection in vivo and that the combination of DATEM-C 12 and monoglyceride provided the greatest bactericidal activity.

EXAMPLE 2

Bactericidal Effects of Diacetyltartaric Acid Esters of Mono- and Diglycerides on *Haemophilus Influenzae*

The bactericidal effects of diacetyltartaric acid esters of mono- and diglycerides against *H. influenzae* were determined in vitro using the procedures set forth above in Example 1. The results of these studies are summarized below in Table 4.

TABLE 4

DATEM-C12 INHIBITS *H. INFLUENZAE* GROWTH

| Treatment | Concentration (μg/ml) | $Log_{10}$ Count/Reduction | Temperature |
|---|---|---|---|
| 66% Similac ® RTF | 0 | 6.8/ no reduction | 37° C. |
| DATEM-C12 | 2400 | 0/6.8 log reduction | 37° C. |
| DATEM-C12 + C12 MG | 1200/3300 | 0/6.8 log reduction | 37° C. |
| DATEM-C12 + C12 MG | 1200/3300 | 6.8/ no reduction | 22° C. |

The data in Table 4 show that diacetyltartaric acid esters of mono- and diglycerides are effective bactericidal agents against *H. influenzae*. In addition, when a 90% Similac® RTF formula was used, diacetyltartaric acid esters of mono- and diglycerides were found to be inactive against *H. influenzae.*

EXAMPLE 3

Bactericidal Effects of Diacetyltartaric Acid Esters of Mono- and Diglycerides on *Helicobacter pylori*

The bactericidal effects of diacetyltartaric acid esters of mono- and diglycerides on *H. pylori* were studied in vitro using the procedure as described below.

MIC, minimum inhibitory concentration, was determined by adding a series of concentrations of the test compound to the *H. pylori* culture medium. After a 5 day incubation period at 37° C., *H. pylori* growth was judged by opacity of the culture medium. When 50% Similac® was used, the MIC could not be determined. MBC, minimum bactericidal concentration, was determined by adding test compound to *H. pylori* medium and incubating at 37° C. for 4 hours. An aliquot of the mixture was plated in *H. pylori* culture media. The end point was bacterial growth.

The results of these studies are summarized below in Table 5.

TABLE 5

THE MIC AND MBC OF DATEM-C12 AGAINST *H. PYLORI*

| Organism | MIC/MBC Broth[a] (μg/ml) | MIC/MBC in 50% Similac[b] (μg/ml) | Similac ® only (% dilution) |
|---|---|---|---|
| *H. pylori* 2597 | 19.5/39.1 | ND*/19.5 | 25%, no inhibition<br>50%, slight inhibition |
| *H. pylori* 3921 | 78.1/78.1 | ND*/78.1 | 50%, no inhibition |

ND = not done.
[a,b]MIC, minimum inhibitory concentration; MBC, minimum bactericidal concentration. Because MIC is judged by cleanless of the culture medium, MIC cannot be judged in 50% Similac ®. The MBC can be determined because a liquid of the mixture is plated in culture media and the end point is bacterial growth.

The data in Table 5 show that DATEM-C12's MIC (minimum inhibitory concentration) and MBC (minimum bactericidal concentration) in the bacterial culture medium and in Similac® indicate that diacetyltartaric acid esters of mono- and diglycerides are strong compounds in inhibiting *H. pylori*. The data also show that Similac® does not affect DATEM-C12's bactericidal activity against *H. pylori.*

EXAMPLE 4

Inhibition of Respiratory Syncytial Virus Infection in HEp-2 Cells

HEp-2, human laryngeal epidermal carcinoma cells were obtained from the American Type Culture Collection (Rockville, Md.). HEp-2 cells seeded at a density of 10,000 cells per well in a 96 well plate (Costar, Cambridge, Mass.) were cultured in Dulbecco's Modified Eagle's (DME) medium supplemented with 10% fetal bovine serum (FBS). The HEp-2 plates were incubated for two days at 37° C. in a humidified incubator in a 5% $CO_2$:95% air atmosphere until the monolayers were confluent. RSV stock and test sample prepared at two times their desired final concentrations were pre-mixed at equal volumes and incubated for 1 hour at 2–8° C. Virus stock was prepared to yield approximately 90% cell death in control wells which contained no virus inhibitors. 100 $\mu$l of virus/test sample mixture were added to wells containing HEp-2 monolayers previously washed in serum free minimal essential medium. The pre-incubation mixture was allowed to absorb onto the cell monolayer for two hours and then removed and replaced with serum-free minimal essential medium. The cell/virus plates were incubated at 37° C. for 4 days before quantification of virus induced cytopathic effect.

Cell survival, quantified spectrophotometrically in each well, was determined by adding 100 $\mu$l of a 20% solution of Alamar Blue dye over the virus inoculum. Alamar Blue dye measures the metabolic activity of living cells employing an oxidation/reduction color indicator that measures metabolic reduction of the growth medium. Cell metabolic activity is indicated by a color change from blue to red. Plates incubated for 4 hours at 37° C. were read on a Molecular Devices (Menlo Park, Calif.) plate reader using a dual endpoint format at 570 nm subtracting the 600 nm wavelength. The percent cell survival correlates directly to the percent virus inhibition by the sample. The percent cell survival in each well was calculated based upon the no virus cell control. Each sample was tested using replicates of four wells. Control wells containing no test agent with and without virus were completed in replicates of eight wells.

Test Agents

Monoglyceride of unhydrogenated sunflower oil was obtained from Eastman Chemical as Myverol 18–92 distilled glycerol monolinoleate containing, by assay, 90% monoester derived from sunflower oil with a fatty acid distribution of 7.0% glycerol monopalmitate, C16:0; 4.5% glycerol monostereate, C18:0; 18.7% glycerol monooleate, C18:1; 67.5% glycerol monolinoleate, C18:2. Monoglyceride C12:0, was obtained from Grinsted Division of Danisco containing a minimum of 90% monoester of C12:0.

DATEM SOY, Panodan FDP Kosher was obtained from Danisco Ingredients, Grinsted Division. It is derived from fully hydrogenated soybean oil (U.S. DATEM SPECIFICATIONS). DATEM PALM, Myvatem 35, was obtained from Eastman Chemical Co. It is derived from fully hydrogenated palm oil (U.S. DATEM SPECIFICATIONS). DATEM SUNF, SDK was obtained from Danisco Ingredients, Grinsted Division. SDK is derived from unhydrogenated sunflower oil (U.S. DATEM SPECIFICATIONS). DATEM BEEF was obtained from Henkel Corp. and is derived from fully hydrogenated beef tallow (EUROPEAN DATEM SPECIFICATIONS). DATEM-C12 was obtained from Danisco Ingredients and is derived from 90% $C_{12}$ monoglyceride. DATEM-C08 was obtained from Danisco Ingredients and is derived from 90% $C_8$ monoglyceride which was obtained from Hullis America.

The various test agents were prepared by adding the test compound to various forms of an infant nutritional product (Similac®). The samples were hand shaken and then retorted utilizing a Steritort continuous sterilizer simulator (FMC, Princeton, N.J.) at a minimum product temperature of 258° F. and $F_o$ greater than or equal to 6. The Steritort system utilizes a gradient water preheat, followed by a saturated steam cook, and a gradient water cool. All cycles were continuously agitated. CaiTageenan (previously found to contain anti-RSV activity) was removed from the formulation to allow testing of the agents. The pre-incubation mixture was allowed to absorb onto the cell monolayer for two hours and then removed and replaced with serum-free minimal essential medium. The results of these cell culture studies are summarized below in Table 6.

TABLE 6

INHIBITION OF RSV BY LIPID AGENTS IN INFANT FORMULA MATRIX (SIMILAC®)

| TEST AGENT | CONCENTRATION ($\mu$g/ml) | PERCENT INHIBITION |
|---|---|---|
| DATEM SOY | 1825 | 98 |
| | 608 | 0 |
| | 203 | −17 |
| | 68 | −13 |
| | 23 | −12 |
| | 7.4 | −12 |
| DATEM PALM | 1825 | 84 |
| | 912 | 36 |
| | 456 | 11 |
| | 228 | 1 |
| | 114 | 2 |
| | 57 | 10 |
| DATEM SUNF | 1825 | 99 |
| | 912 | 100 |
| | 456 | 34 |
| | 228 | 5 |
| | 114 | −8 |
| | 57 | −3 |
| DATEM BEEF | 1825 | 100 |
| | 912 | 100 |
| | 456 | 52 |
| | 228 | −3 |
| | 114 | −5 |
| | 57 | 0 |
| DATEM-C12 | 1825 | 99 |
| | 912 | 100 |
| | 456 | 42 |
| | 228 | −9 |
| | 114 | −8 |
| | 57 | −13 |
| DATEM-C08 | 1825 | 78 |
| | 912 | −14 |
| | 456 | −6 |
| | 228 | −6 |
| | 114 | −4 |
| | 57 | −5 |
| $C_{18}$ MONOGLYCERIDE* | 229 | −8 |
| | 115 | −13 |
| | 57 | −18 |
| | 29 | −21 |
| | 0 | −22 |
| MONOGLYCERIDE $C_{12}$ | 1000 | 96 |
| | 500 | 42 |
| | 250 | 2 |
| | 125 | −18 |
| | 63 | −16 |

*Monoglyceride C18:0 mixed with equal weight of soy fatty acid to aid in solubility. The listed concentration is that of monoglyceride only.

The data in Table 6 were obtained using a 1:1 mixture of infant formula and virus in diluted cell culture. These data show that diacetyltartaric acid esters of mono- and diglycerides have significant anti-RSV activity in an infant nutritional formula that contains protein. To assure that anti-RSV activity would not disappear in full strength infant formula, additional studies were preformed whereby the virus was diluted directly into infant formula in place of cell culture medium and the virus neutralization assay performed as described above. All diacetyltartaric acid esters of mono- and diglycerides, with the exception of those derived from $C_8$ monoglyceride, retained activity in infant formula.

To compare the anti-RSV activity of different forms of diacetyltartaric acid esters of mono- and diglycerides, the DATEM suppliers were asked to make 4 forms of diacetyltartaric acid esters of mono- and diglycerides differing in the length and saturation of fatty acid chains by using different oils. These diacetyltartaric acid esters of mono- and diglycerides forms were: DATEM-C12:0, DATEM-PALM OIL, DATEM-SUNFLOWER OIL, and DATEM-SOY. The forms of diacetyltartaric acid esters of mono- and diglycerides were mixed individually into Similac® and the activity against RSV infectivity was determined as described above. The results of these studies are summarized in Table 7 below.

TABLE 7

DIFFERENT FORMS OF DATEM ON RSV INFECTIVITY IN SIMILAC ®

| Forms of DATEM | $IC_{50}$ in Similac ® (μg/ml) |
|---|---|
| DATEM-C12:0 | 450 |
| DATEM-Soy (C18:0/C16:0) | 110 |
| DATEM-Sunflower (C18:2) | 540 |
| DATEM-Palm (C16:0) | 1120 |

The data in Table 7 show that diacetyltartaric acid esters of mono- and diglycerides made from the different fats all have inhibitory activity against RSV infection in infant formula.

EXAMPLE 5

In vivo Prevention of RSV Infection in Cotton Rats

Cotton rats have been used as an RSV research animal model for about 20 years. The cotton rat has a similar pathological change in the lung to that observed in human infants when infected by RSV (Prince et al., 1978). Also, RSV vaccine-treated cotton rats develop severe histological damage when exposed to RSV, which is similar to what occurs in human infants (Prince et al., 1986). It has also been observed that the intravenously-administered RSV-IgG has to reach a titer of ≧1:100 concentration to show the preventive effect (Prince et al., 1985). The same serum concentration of RSV-IgG in human infants is protective (Groothuis et al., 1993, 1995). Due to these similarities, the FDA has recommended the cotton rat as an appropriate model for RSV studies.

To have a repeatable RSV nasal and lung infection, a high RSV dose ($10^4$ pfu/animal) was intra-nasally inoculated to all animals. The inoculum (100 μl) consisted of 50 μl of RSV stock solution and 50 μl of test product. The test products, diacetyltartaric acid esters of mono- and diglycerides, monoglyceride (MG) and carrageenan, were suspended respectively in an infant formula that did not contain carrageenan, soy lecithin, or Myverol (a modified Similac®, or M. Similac®). In addition, some studies were performed in an infant formula in which the intact protein was replaced with a casein hydrolysate (Alimentum®). All animals consumed the regular rodent chow diet throughout the experimental period. Four days after RSV challenge, all animals were sacrificed. Their lung and nasal tissue were isolated for determination of RSV titers. As a positive control, a 5% RSV-IgG was always used. Anegative control group (without any treatment before and after RSV challenge) was also employed for each experiment. RSV titers in the lung and nasal tissues from the negative control group must be at the regular high level to validate the data. Also, a very low RSV titer in the lung and nasal tissues from the positive control group was used to validate the experiment data. The results of these studies are summarized in Table 8 below.

TABLE 8

DATEM (C18:0/C16:0) INHIBITION OF RSV INFECTION IN COTTON RATS

| Treatment | # of Rats | RSV titer in Lung ($Log_{10}$ PFU/g tissue) | RSV titer in Nose ($Log_{10}$ PFU/g tissue) |
|---|---|---|---|
| Negative Control | 12 | 3.05 ± 0.28 | 4.20 ± 0.25 |
| IgG Positive Control | | 100% inbibition | 100% inhibition |
| Formula Control (M. Similac ®)* | 12 | $3.22 \pm 0.19^A$ | $3.21 \pm 0.70^a$ |
| DATEM in M. Similac ® (1825 mg/L) | 12 | $3.23 \pm 0.24^A$ | $2.90 \pm 0.68^a$ |
| DATEM in M. Similac ® (3650 mg/L) | | $2.68 \pm 0.41^B$ | $2.00 \pm 0.66^b$ |
| DATEM 1825 mg/L + MG 3650 mg/L in M. Similac ® (DATEM & MG pre-mix with water) | 12 | $2.50 \pm 0.40^B$ | 100% inhibition$^b$ |
| DATEM 1825 mg/L + MG 3650 mg/L in M. Similac ® (DATEM & MG pre-mix with oil) | 12 | $2.69 \pm 0.41^B$ | 100% inhibition$^b$ |
| DATEM 1825 mg/L + MG 5000 mg/L in M. Similac ® (DATEM & MG pre-mix with water | 11 | $2.50 \pm 0.40^B$ | 100% inhibition$^b$ |
| DATEM in Alimentum ® Powder (1825 mg/L) | 6 | $2.72 \pm 0.31^B$ | $2.31 \pm 0.51^b$ |
| 1000 mg/L Carrageenan in M. Similac ® | 11 | $3.06 \pm 0.16^A$ | $3.78 \pm 0.47^a$ |

*This formula control was used as a base for comparison with other treatment groups. Values in a column labeled with a different superscript letter differ at $P < 0.05$.

The data from Table 8 show that diacetyltartaric acid esters of mono- and diglycerides inhibit RSV infection in vivo. The data also show that diacetyltartaric acid esters of mono- and diglycerides and MG act synergistically to inhibit RSV activity. Pre-mixing diacetyltartaric acid esters of mono- and diglycerides and MG in water or in oil does not result in a difference in anti-RSV activity. Diacetyltartaric acid esters of mono- and diglycerides are effective virucides in infant nutritional products both in the presence (Similac®) and absence (Alimentum®) of intact protein.

EXAMPLE 6

Inhibition of RSV Infection in HEp-2 Cells by Water-miscible Lipid Derivatives in Aqueous Solvent HEp-2, human laryngeal epidermal carcinoma cells were obtained from the American Type Culture Collection (Rockville, Md.). HEp-2 cells seeded at a density of 10,000 cells per well in a 96 well plate (Costar, Cambridge, Mass.) were cultured in Dulbecco's Modified Eagle's (DME) medium supplemented with 10% fetal bovine serum (FBS). The HEp-2 plates were incubated for two days at 37° C. in a humidified incubator in a 5% $CO_2$:95% air atmosphere until the monolayers were confluent. RSV stock and test sample prepared at two times their desired final concentrations were pre-mixed at equal volumes and incubated for 1 hour at 2–8° C. Virus stock was prepared to yield approximately 90% cell death in control wells which contained no virus inhibitors. 100 $\mu$l of virus/test sample mixture were added to wells containing HEp-2 monolayers previously washed in serum free minimal essential medium. The cell/virus plates were incubated at 37° C. for 4 days before quantification of virus induced cytopathic effect.

Cell survival, quantified spectrophotometrically in each well, was determined by adding 100 $\mu$l of a 20% solution of Alamar Blue dye over the virus inoculum. Alamar Blue dye measures the metabolic activity of living cells employing an oxidation/reduction color indicator that measures metabolic reduction of the growth medium. Cell metabolic activity is indicated by a color change from blue to red. Plates incubated for 4 hours at 37° C. were read on a Molecular Devices (Menlo Park, Calif.) plate reader using a dual endpoint format at 570 nm subtracting the 600 nm wavelength. The percent cell survival correlates directly to the percent virus inhibition by the sample. The percent cell survival in each well was calculated based upon the no virus cell control. Each sample was tested using replicates of four wells. Control wells containing no test agent with and without virus were completed in replicates of eight wells.

Test Agents

Monoglyceride of unhydrogenated sunflower oil was obtained from Eastman Chemical as Myverol 18–92 distilled glycerol monolinoleate containing, by assay, 90% monoester derived from sunflower oil with a fatty acid distribution of 7.0% glycerol monopalmitate, C16:0; 4.5% glycerol monostereate, C18:0; 18.7% glycerol monooleate, C18: 1; 67.5% glycerol monolinoleate, C18:2. Monoglyceride C12:0, was obtained from Grinsted Division of Danisco containing a minimum of 90% monoester of C12:0. DATEM SOY, Panodan FDP Kosher was obtained from Danisco Ingredients, Grinsted Division. It is derived from fully hydrogenated soybean oil (U.S. DATEM SPECIFICATIONS). DATEM PALM, Myvatem 35, was obtained from Eastman Chemical Co. It is derived from fully hydrogenated palm oil (U.S. DATEM SPECIFICATIONS). DATEM SUNF, SDK was obtained from Danisco Ingredients, Grinsted Division. SDK is derived from unhydrogenated sunflower oil (U.S. DATEM SPECIFICATIONS). DATEM BEEF was obtained from Henkel Corp. and is derived from fully hydrogenated beef tallow (EUROPEAN DATEM SPECIFICATIONS). DATEM-C12 and DATEM-C08 were derived from a 90% $C_{12}$-monoglyceride and a 90% $C_8$ monoglyceride, respectively. These two forms of diacetyltartaric acid esters of mono- and diglycerides were made by Danisco Ingredients, Grinsted Division, under a specific request from Ross Products Division of Abbott Laboratories.

The various test agents were prepared by adding the test compound to phosphate buffered saline (PBS). The samples were hand shaken and then retorted utilizing a Steritort continuous sterilizer simulator (FMC, Princeton, N.J.) at a minimum product temperature of 258° F. and $F_o$ greater than or equal to 6. The Steritort system utilizes a gradient water preheat, followed by a saturated steam cook, and a gradient water cool. All cycles were continuously agitated. The results of cell culture studies using diacetyltartaric acid esters of mono- and diglycerides in PBS are summarized below in Table 9.

TABLE 9

TEST COMPOUNDS IN PBS INHIBIT RSV INFECTION IN VITRO

| TEST AGENT | CONCENTRATION ($\mu$g/ml) | PERCENT INHIBITION |
|---|---|---|
| Monoglyceride | 2.2 | 99 |
| Sunflower (in 2% | 1.1 | 23 |
| ethanol) | 0.55 | 15 |
| | 0 | 17 |
| Monoglyceride C12:0 | 10 | 44 |
| | 2 | 35 |
| | 0.4 | 19 |
| | 0 | 11 |
| DATEM SOY | 10 | 98 |
| | 3 | 83 |
| | 1 | 36 |
| | 0.3 | 8 |
| | 0 | 12 |
| DATEM PALM | 10 | 100 |
| | 3 | 97 |
| | 1 | 83 |
| | 0.3 | 12 |
| | 0 | 12 |
| DATEM SUNF | 10 | 99 |
| | 3 | 94 |
| | 1 | 58 |
| | 0.3 | 12 |
| | 0 | 12 |
| DATEM BEEF | 10 | 100 |
| | 3 | 98 |
| | 1 | 73 |
| | 0.3 | 40 |
| | 0 | 12 |

The data in Table 9 show that unhydrogenated sunflower oil derived monoglyceride $C_8$, monoglyceride $C_{12}$ and diacetyltartaric acid esters of mono- and diglycerides derived from several sources all inhibit the infection of mammalian cells by RSV in a dose-dependent manner.

Additional studies were performed to determine the synergistic anti-viral effects of diacetyltartaric acid esters of mono- and diglycerides, lipophilic monoglycerides (MG) and carrageenan. These studies were carried out using LLC-MKC cells and PBS as the diluent. The results of these studies are summarized below in Table 10. The RSV inhibition assay semi-quantitatively determines the ability of a test material (antibody or other bioactive compound) to inhibit the infection of monkey kidney cells (LLC-MK2) by human respiratory syncytial virus (RSV). Infected cells are identified using an immunoperoxidase method and counted. The method is performed in a microtiter format and is described briefly below:

LLC-MK2 rhesus monkey kidney cells were obtained from the American Type Culture Collection and were cultured in Eagles modified essential medium (EMEM) supplemented with 10% fetal bovine serum. For RSV inhibition assays, LLC-MK2 cells at 5,000 cells/well were seeded into fibronectin treated microtiter plates and incubated for 3–4 days prior to use in the infectivity reduction assay. On the day of assay, stock RSV was diluted in cell culture medium (MEM) to 10–20,000 infected cell units (ICU)/mL, and added to an equal volume (200 μl) of serially diluted sample preparations at suitable concentrations. Mixtures of diluted test samples and virus were then incubated for 2 hours at 4° C. prior to adding to LLC-MK2 cells. Prior to the addition of the virus—test sample inoculum to microtiter plates, culture medium was removed and the monolayers rinsed one time with EMEM. All sample-virus dilutions were tested in triplicate wells. The virus—test sample inoculum mixture was allowed to adsorb to LLC-MK2 monolayers for 2 hours at 37° C. in a humidified $CO_2$ incubator. Following incubation, 150 μL of EMEM was added to all wells and the plates incubated at 37° C. for 16 hours in the $CO_2$ incubator. After incubation, the culture medium was removed and the monolayers fixed with cold ethanol (70% then 100%). After fixing, microtiter plates were rinsed once with 200 μl/well Dulbecco's PBS, and diluted bovine anti-RSV antibody (200 μL) added to all wells. Following a 30 minute incubation at room temperature and 3 rinses with PBS/0.5% chick egg albumen (PBS/CEA), peroxidase labeled rabbit anti-bovine IgG was added to all wells and incubated at room temperature for 30 minutes. Microtiter plates were then rinsed 3 times with PBS/CEA and diaminobenzadine substrate added and incubated for 20 minutes. Plates were then rinsed as above with PBS/CEA, and the number of stained RSV-infected cells (IC) per well determined using an inverted microscope. The number of ICs' in triplicate wells was compared with the number of ICs' of virus control wells (mean of 9)and the percent inhibition (PI) calculated; [PI=1.0–[Mean ICs' per well of test sample/Mean ICs' per well of virus control]. A positive control preparation (bovine and RSV serum) was run on each microtiter plate. Results from RSV inhibition testing are reported as the concentration of the test material (μg/ml) that yields a 50% reduction in RSV infected cell count ($IC_{50}$) as shown in Table 10.

TABLE 10

OTHER COMPOUNDS INFLUENCE DATEM'S ANTI-RSV ACTIVITY IN VITRO

| Combination of 3 compounds | DATEM $IC_{50}$ (μg/ml) | Enhancement Factor |
|---|---|---|
| | DATEM $IC_{50}$ | |
| DATEM | 3.93 | 1.0 |
| DATEM + MG (0.4 μg/ml) | 1.51 | 2.6 |
| DATEM + Carrageenan (0.1 μg/ml) | 2.56 | 1.5 |
| DATEM + MG (0.4 μg/ml) + Carrageenan (0.05 μg/ml) | 1.5 | 2.6 |
| | MG's $IC_{50}$ | |
| MG alone | 3.11 | 1.0 |
| MG + DATEM (1.4 μg/ml) | 0.43 | 7.2 |
| MG + Carrageenan (0.1 μg/ml) | 0.80 | 3.9 |
| MG + DATEM (1.4 μg/ml) + Carrageenan (0.05 μg/ml) | 0.44 | 7.1 |
| | Carrageenan's $IC_{50}$ | |
| Carrageenan alone | 3.93 | 1.0 |
| Carrageenan + DATEM (1.4 μg/ml) | 1.51 | 2.6 |
| Carrageenan + MG (0.8 μg/ml) | 2.56 | 1.5 |
| Carrageenan + DATEM (1.4 μg/ml) + MG (0.4 μg/ml) | 1.5 | 2.6 |

The data in Table 10 show that combinations of diacetyltartaric acid esters of mono- and diglycerides and MG or diacetyltartaric acid esters of mono- and diglycerides and carrageenan have increased anti-RSV activity. Diacetyltartaric acid esters of mono- and diglycerides enhance the uniform distribution of MG in the PBS system and this likely explains the synergy.

To compare the anti-RSV activity of different forms of diacetyltartaric acid esters of mono- and diglycerides, the DATEM suppliers were asked to make 5 forms of diacetyltartaric acid esters of mono- and diglycerides differing in the length and saturation of fatty acid chains by using different oils. These diacetyltartaric acid esters of mono- and diglycerides forms were: DATEM-C12:0, DATEM-PALM OIL, DATEM-BEEF TALLOW, DATEM-SUNFLOWER OIL, and DATEM-SOY. The forms of diacetyltartaric acid esters of mono- and diglycetides were mixed individually into PBS and the activity against RSV infectivity was determined as described above. The results of these studies are summarized in Table 11 below.

TABLE 11

THE IN VITRO ANTI-RSV ACTIVITY OF DIFFERENT FORMS OF DATEMs

| Forms of DATEM | $IC_{50}$ (μg/ml) |
|---|---|
| C:12 DATEM | 14.74 |
| C:18 DATEM-SOY | 2.10 |
| C:18 DATEM-SUNFLOWER 18:2) | 0.80 |
| DATEM-PALM | 3.01 |
| DATEM-animal fat (European) (Tartaric acid/24% in DATEM) | 0.90 |

The data in Table 11 show that diacetyltartaric acid esters of mono- and diglycerides made from the different fats all have inhibitory activity against RSV infection.

What is claimed is:

1. A pharmaceutical composition comprising an amount of diacetyltartaric acid esters of mono- and diglycerides effective to inhibit the infectious activity of a bacteria and a physiologically acceptable diluent.

2. The composition of claim 1 wherein the diacetyltartaric acid esters of mono- and diglycerides are obtained from soy oil, palm oil, sunflower oil, beef tallow or a $C_8$–$C_{20}$ monoglyceride.

3. The composition of claim 1 wherein the diacetyltartaric acid esters of mono- and diglycerides correspond to Formula I, below:

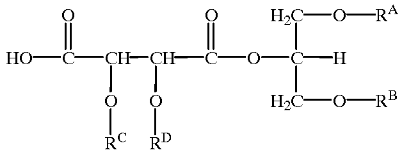

(I)

where $R^A$ is a $C_8$–$C_{24}$ fatty acid, $R^B$ is H, $R^C$ and $R^D$ are acetyl, and wherein 90 percent or more of the total fatty acid content is in the form of a single fatty acid.

4. The composition of claim 3 wherein $R^A$ is a $C_{10}$–$C_{20}$ fatty acid.

5. The composition of claim 3 wherein $R^A$ is a $C_{12}$–$C_{18}$ fatty acid.

6. The composition of claim 3 wherein $R^A$ is a $C_{12}$ fatty acid.

7. The composition of claim 3 wherein the $C_8$–$C_{24}$ fatty acid is saturated, unsaturated, or hydroxylated.

8. The composition of claim 1 wherein the physiologically acceptable carrier is an aqueous solvent.

9. The composition of claim 8 further comprising an effective bactericidal or virucidal amount of one or more monoglycerides having an HLB value less than about 6.

10. The composition of claim 4 that is formulated as an aerosol spray.

11. A process for inhibiting an infection caused by a bacteria in a subject in need of such treatment comprising administering to the subject a bactericidal amount of diacetyltartaric acid esters of mono- and diglycerides.

12. The process of claim 11 wherein the bacterial infection is caused by bacteria of the genus Streptococcus, Haemophilus, or Helicobacter.

13. The process of claim 12 wherein the bacteria is *Streptococcus pneumoniae, Haemophilus influenzae*, or *Helicobacter pylori.*

14. The process of claim 11 wherein the diacetyltartaric acid esters of mono- and diglycerides are obtained from soy oil, palm oil, sunflower oil, or beef tallow.

15. The process of claim 11 wherein the diacetyltartaric acid esters of mono- and diglycerides correspond to Formula I, below:

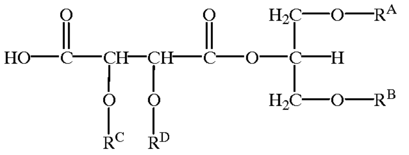

(I)

where $R^A$ is a $C_8$–$C_{24}$ fatty acid, $R^B$ is H, $R^C$ and $R^D$ are acetyl, and wherein 90 percent or more of the total fatty acid content is in the form of a single fatty acid.

16. The process of claim 15 wherein $R^A$ is a $C_{10}$–$C_{20}$ fatty acid.

17. The process of claim 15 wherein $R^A$ is a $C_{12}$–$C_{18}$ fatty acid.

18. The process of claim 15 wherein $R^A$ is a $C_{12}$ fatty acid.

19. The process of claim 15 wherein the $C_8$–$C_{24}$ fatty acid is saturated.

20. The process of claim 15 wherein the diacetyltartaric acid esters of mono- and diglycerides are contained in an aqueous solvent.

21. The process of claim 20 wherein the aqueous solvent further comprises an effective bactericidal or virucidal amount of one or more monoglycerides having an HLB value less than about 6.

* * * * *